(12) United States Patent
Jacob et al.

(10) Patent No.: US 10,028,909 B2
(45) Date of Patent: *Jul. 24, 2018

(54) RAPIDLY DISPERSIBLE DOSAGE FORM OF OXCARBAZEPINE

(71) Applicant: APRECIA PHARMACEUTICALS COMPANY, Langhorne, PA (US)

(72) Inventors: Jules Jacob, Yardley, PA (US); Kelly Caputo, Langhorne, PA (US); Micael Guillot, Lansdale, PA (US); Kenneth J. Sultzbaugh, Bridgewater, NJ (US); Thomas G. West, Lawrenceville, NJ (US)

(73) Assignee: APRECIA PHARMACEUTICALS LLC, Blue Ash, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/437,966

(22) Filed: Feb. 21, 2017

(65) Prior Publication Data

US 2017/0172919 A1 Jun. 22, 2017

Related U.S. Application Data

(63) Continuation of application No. 15/045,711, filed on Feb. 17, 2016, now Pat. No. 9,616,018, which is a continuation of application No. 14/837,493, filed on Aug. 27, 2015, now Pat. No. 9,314,429, which is a continuation of application No. PCT/US2014/028125, filed on Mar. 14, 2014.

(60) Provisional application No. 61/791,726, filed on Mar. 15, 2013.

(51) Int. Cl.
| | |
|---|---|
| A61K 9/16 | (2006.01) |
| A61K 9/00 | (2006.01) |
| A61K 31/55 | (2006.01) |
| A61K 9/20 | (2006.01) |
| A61K 9/70 | (2006.01) |
| B33Y 10/00 | (2015.01) |
| B33Y 70/00 | (2015.01) |
| B33Y 80/00 | (2015.01) |
| B29C 64/165 | (2017.01) |
| B29K 105/00 | (2006.01) |

(52) U.S. Cl.
CPC .......... *A61K 9/0056* (2013.01); *A61K 9/1611* (2013.01); *A61K 9/1617* (2013.01); *A61K 9/1623* (2013.01); *A61K 9/1635* (2013.01); *A61K 9/1652* (2013.01); *A61K 9/1694* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/7007* (2013.01); *A61K 31/55* (2013.01); *B29C 64/165* (2017.08); *B33Y 10/00* (2014.12); *B33Y 70/00* (2014.12); *B33Y 80/00* (2014.12); *B29K 2105/0035* (2013.01); *B29K 2105/0058* (2013.01); *B29K 2105/251* (2013.01)

(58) Field of Classification Search
CPC .... A61K 31/55; A61K 9/0056; A61K 9/1611; A61K 9/1617; A61K 9/1623; A61K 9/1635; A61K 9/1652; A61K 9/2009; A61K 9/2013; A61K 9/2018; A61K 9/2027; A61K 9/2054
See application file for complete search history.

(56) References Cited

U.S. PATENT DOCUMENTS

| | | |
|---|---|---|
| 4,371,516 A | 2/1983 | Gregory |
| 4,642,903 A | 2/1987 | Davies |
| 4,855,326 A | 8/1989 | Fuisz |
| 5,178,878 A | 1/1993 | Wehling |
| 5,283,065 A | 2/1994 | Doyon |
| 5,380,473 A | 1/1995 | Bogue |
| 5,518,730 A | 5/1996 | Fuisz |
| 5,578,322 A | 11/1996 | Shiozawa |
| 5,607,697 A | 3/1997 | Alkire |
| 5,631,023 A | 5/1997 | Kearney |
| 5,738,875 A | 4/1998 | Yarwood |
| 6,106,861 A | 8/2000 | Chauveau |
| 6,136,347 A | 10/2000 | Pollinger |
| 6,471,992 B1 | 10/2002 | Yoo |
| 6,482,823 B1 | 11/2002 | Yu |
| 6,586,012 B2 | 7/2003 | Yu |
| 6,767,557 B2 | 7/2004 | Ulrich |
| 7,749,533 B2 | 7/2010 | Fu |
| 7,897,173 B2 | 3/2011 | Ziegler |
| 7,906,141 B2 | 3/2011 | Ziegler |
| 2003/0133975 A1 | 7/2003 | Yoo |
| 2006/0039981 A1 | 2/2006 | Murpani |
| 2006/0127479 A1 | 6/2006 | Kumaraperumal |

(Continued)

FOREIGN PATENT DOCUMENTS

| | | |
|---|---|---|
| WO | 9836738 A1 | 8/1998 |
| WO | 2006070406 A1 | 7/2006 |
| WO | 2007089247 A1 | 8/2007 |

OTHER PUBLICATIONS

Yu et al. ("A novel fast disintegrating tablet fabricated three-dimensional printing" in Drug Development and Indust. Pharm. (2009), 35(12), 1530-1536.

*Primary Examiner* — Ernst V Arnold
(74) *Attorney, Agent, or Firm* — Innovar, L.L.C.; Rick Matos

(57) ABSTRACT

A high dose orodispersible dosage form of oxcarbazepine is provided. Drug-containing particles of oxcarbazepine are included within a porous bound matrix. The dosage form disperses in saliva or water in less than 15 sec and it has sufficient hardness to withstand handling and storage. It can be used to treat diseases or disorders that are therapeutically responsive to oxcarbazepine or a derivative thereof.

26 Claims, 1 Drawing Sheet

(56) References Cited

U.S. PATENT DOCUMENTS

| | | |
|---|---|---|
| 2006/0159758 A1 | 7/2006 | Gandhi |
| 2006/0182796 A1 | 8/2006 | Wu et al. |
| 2007/0092553 A1 | 4/2007 | Tengler et al. |
| 2007/0154550 A1 | 7/2007 | Arti |
| 2007/0218129 A1 | 9/2007 | Besse |
| 2007/0248684 A1 | 10/2007 | Blau |
| 2010/0278901 A1 | 11/2010 | Tengler et al. |
| 2010/0285130 A1 | 11/2010 | Sanghvi |
| 2011/0212171 A1 | 9/2011 | Venkatesh et al. |
| 2012/0040001 A1 | 2/2012 | Koizumi |
| 2012/0076858 A1 | 3/2012 | Kolter |
| 2012/0207836 A1 | 8/2012 | General |
| 2012/0207929 A1 | 8/2012 | Yoo |

RAPIDLY DISPERSIBLE DOSAGE FORM OF OXCARBAZEPINE

CROSS-REFERENCE TO EARLIER FILED APPLICATIONS

The present application claims the benefit of and is a continuation of Ser. No. 15/045,711 filed Feb. 17, 2016, which is a continuation of Ser. No. 14/837,493 filed Aug. 27, 2015, now U.S. Pat. No. 9,314,429 issued Apr. 19, 2016, which is a continuation of PCT/US2014/028125 filed Mar. 14, 2014, which claims the benefit of provisional application 61/791,726 filed Mar. 15, 2013, the entire disclosures of which are hereby incorporated by reference.

FIELD OF THE INVENTION

The present invention concerns a rapidly dispersing (orodispersible) solid oral dosage form of oxcarbazepine. In particular, the dosage form disperses within a period of less than about ten seconds when placed in the mouth of a subject. The invention also relates to methods of use of the dosage form for the treatment of diseases, disorders or conditions that are therapeutically responsive to oxcarbazepine or a derivative thereof. A process for preparing the dosage form is also provided.

BACKGROUND OF THE INVENTION

Solid oral dosage forms containing oxcarbazepine (OXC; 10,11-Dihydro-10-oxo-5H-dibenz[b,f]azepine-5-carboxamide; disclosed in U.S. 2004-0044200A1, U.S. Pat. No. 3,642,775 and U.S. Pat. No. 3,716,640) are known (FDA Electronic Orange Book). OXC is susceptible to hydrolysis under basic/alkaline conditions. Oxcarbazepine is a prodrug that is quickly reduced to a 10-monohydroxy metabolite derivative (MHD) which is the active metabolite.

OXC is an antiepileptic indicated for use as monotherapy or adjunctive therapy in the treatment of partial seizures in adults and as monotherapy in the treatment of partial seizures in children aged 4 years and above with epilepsy, and as adjunctive therapy in children aged 2 years and above with epilepsy.

OXC is hydrophobic and poorly water soluble and must be present in very small particles sizes when administered as a solid oral dosage form in order to provide sufficient absorption of drug. U.S. Pat. No. 7,037,525 specifies oxcarbazepine having a particle size such that the maximum residue on a 40 micron sieve is less than or equal to 5% and the median particle size is approximately 2 to 12 microns, or 4 to 10 microns or 6 to 8 microns. EP 2,010,499 A1 discloses oxcarbazepine having a particle size distribution with a D[v,0.5] value of between about 15 microns to about 30 microns and a D[v,0.9] value of less than or equal to 90 microns. U.S. Pat. No. 8,119,148 discloses OXC wherein the quantity of particles larger than 40 micrometers (μm) is limited to a maximum of 5% by weight and the median particle size by Fraunhofer diffraction is specified to be within 4-10 μm. EP 2,077,822 discloses OXC with a median particle size of 4-10 μm. PCT Publication WO 2007-007182 discloses OXC with a median particle size in the range of 15 to 30 μm and wherein the composition contains no wetting agent. PCT Publication WO 2006-046105 discloses OXC with a median particle size in the range of 15 to 30 μm and wherein the composition contains no wetting agent. PCT Publication WO 2002-094774 discloses OXC with a median particle size of about 20 μm to about 50 μm with a maximum residue of about 10% on a 45 μm to up to 100 μm sieve and wherein a wetting agent is present. Indian Application No. 1186/MUM/2004 discloses a pharmaceutical composition containing oxcarbazepine particles and meglumine, which aids in dissolution of the drug, wherein the oxcarbazepine has a particle size of not less than 50 μm or about 80 to 140 μm. EP 2,146,699 A1 discloses dosage forms containing oxcarbazepine having a median particle size of about 2 μm or less.

OXC is dosed orally according to a twice daily regimen (BID) at doses of 300 to 2400 mg per day for the treatment of epilepsy. When a unit dose includes 150 to 1200 mg of OXC, young and elderly patients typically experience difficulty in swallowing solid oral dosage forms containing such high doses, especially because of the large amount of excipients included in known dosage forms. Difficulty in swallowing leads to poor patient compliance. Attempts to resolve this problem have led to the development of oral liquid formulations. Stability, contamination and inaccurate dosing problems, however, are still associated with such dosage forms.

Given the high doses of OXC required per tablet, it is difficult to formulate rapidly dispersible solid oral dosage forms with sufficient hardness and friability suitable for storage and handling while at the same time providing a dosage form that is small enough for easy swallowing.

Orodispersible dosage forms disperse or disintegrate in the mouth in a minimal amount of saliva or water. Such dosage forms provide ease of swallowing, accuracy of dosing, and rapid therapeutic action. U.S. Pat. No. 7,749,533 to Fu et al. discloses a dosage form containing granules containing a drug, porous plastic substance, water penetration enhancer, binder and drug. The granules must be compressed in order to create the dosage form. U.S. Pat. No. 4,371,516 to Gregory et al. and U.S. Pat. No. 5,738,875 disclose freeze-dried dosage forms. U.S. Pat. No. 5,178,878 to Wehling et al. discloses a soft-compress orodispersible dosage form. Effervescent dosage forms and quick release coatings of insoluble microparticles are described in U.S. Pat. Nos. 5,578,322 and 5,607,697. Freeze dried foams and liquids are described in U.S. Pat. No. 4,642,903 and U.S. Pat. No. 5,631,023. Melt-spun dosage forms are described in U.S. Pat. Nos. 4,855,326, 5,380,473 and 5,518,730. U.S. 20070218129 discloses an immediate release dispersible and orodispersible solid pharmaceutical composition having the form of particles with a size lower than 710 μm upon dispersion into water, wherein the formulation is made by wet granulation; however, the disintegration times range from 53 to 60 sec.

U.S. Pat. No. 6,471,992, U.S. 2012-0207929 and U.S. 2003-0133975 disclose three-dimensionally printed rapidly dispersing dosage forms. Even so, an orodispersible three-dimensionally printed dosage form containing OXC has not been suggested. It is not possible to predict a priori whether a three-dimensionally printed dosage form containing substantial amounts of OXC can be made to disperse in a minimal amount of aqueous fluid in 10 sec or less or 5 sec or less while at the same time possessing sufficient hardness to endure handling and storage.

Very few orodispersible dosage forms containing OXC have been disclosed or suggested. U.S. Pat. No. 8,127,516 and U.S. 20120110957 to Lee suggest a film-coated tablet or film-coated powder fill. U.S. Pat. No. 8,012,505 and U.S. 20040228919 to Houghton suggest a freeze-dried non-compressed fast-dispersing solid dosage form. U.S. Pat. No. 6,709,669 and U.S. Pat. No. 6,509,040 to Murray and U.S. 20040076666 to Green suggest a freeze-dried non-compressed fast-dispersing solid dosage form having fish gelatin as carrier. U.S. 20080312168 to Pilgaonkar discloses a dispersible compressed tablet that disperses in water in three minutes. The tablet contains oxcarbazepine, Copovidone (Kollidon VA 64), microcrystalline cellulose (Avicel PH 102), Sodium starch glycolate (Primojel), Crospovidone (Kollidon CL), Hydroxypropylmethylcellulose (Methocel K100 LV), Hydroxyethylcellulose (Natrosol HHX), Aerosil, Talc and magnesium stearate.

It would be beneficial to provide a rapidly-dispersing solid oral dosage form containing a high concentration of OXC and exhibiting low friability and sufficient hardness to withstand storage and handling while at the same time exhibiting an extremely rapid disintegration rate and acceptable taste; however, no such suitable dosage form has been suggested in the art. In particular, no such three-dimensionally printed dosage form has been suggested.

SUMMARY OF THE INVENTION

The present invention seeks to overcome some or all of the disadvantages inherent in the art. The present invention provides an orodispersible solid dosage form, as described herein, comprising oxcarbazepine as the primary or sole active ingredient, wherein the dosage form comprises a bound matrix that disperses in about 15 sec or less in a volume of about 10 ml or less of water or saliva. The matrix disperses in the mouth of a subject to which it is administered, thereby facilitating swallowing and administration.

The inventors have discovered it is very difficult to produce three-dimensionally printed rapidly-dispersing dosage forms containing a high weight percentage or high amount of small particle size OXC and exhibiting adequate hardness, acceptable surface texture and extremely rapid dispersion/disintegration. Dosage forms made from bulk powder comprising high amounts (percentages) of small native particles of OXC perform poorly; however, OXC must still be included in the dosage form in very small particle size form (as discussed above) in order to ensure adequate absorption in a subject to which it is administered.

In order to resolve this problem, the inventors have discovered that the "effective particle size" of OXC in the bulk powder must be increased without increasing the "actual particle size" of the drug. Doing so permits administration of OXC with an actual particle size suitable for absorption and an effective particle size suitable for use in the bulk powder of a 3DP orodispersible dosage form. The "effective particle size" is increased by including small "native particles" of OXC in "drug-containing particles" in the bulk powder, such that the drug-containing particles are larger in size than the native particles of OXC.

In some aspects, the invention provides a rapidly dispersible, i.e. orodispersible, dosage form and administration thereof for the treatment of diseases, conditions or disorders that are therapeutically responsive to oxcarbazepine. The rapidly dispersible solid dosage form comprises a porous three-dimensionally printed bound orodispersible matrix comprising drug-containing particles of OXC and bulk material comprising at least one disintegrant, at least one surfactant, and at least one binder. The bulk material may further comprise at least one glidant, at least one sweetener and/or at least one flavorant.

The matrix is formed by deposition of a printing fluid to a powder, whereby the particles of the powder become bound by binder. The matrix is porous with a defined overall bulk density, disintegration (dispersion) time in aqueous fluid, dissolution time in aqueous fluid, and moisture content. The matrix provides a balance of sufficient hardness, low friability and extremely rapid dispersion time in a small volume of aqueous liquid.

In some embodiments, OXC is present in crystalline form. All polymorphs thereof are contemplated. The crystallinity of OXC or any other material can be determined by differential scanning calorimetry (DSC) to determine the presence of amorphous material. In some embodiments, OXC is present in amorphous form in the bulk powder or in the matrix.

The invention also provides an orodispersible dosage form comprising a three-dimensionally printed matrix comprising bound sweetener, binder, disintegrant, surfactant, and drug-containing particles of OXC, wherein the binder binds the matrix. The matrix is generally not bound by OXC itself. The printing fluid does not dissolve any substantial amount of OXC during a three-dimensional printing process.

One aspect of the invention provides an orodispersible three-dimensionally printed matrix comprising: OXC, at least one sweetener, at least one binder, at least one disintegrant, at least one surfactant, and at least one glidant; wherein the matrix comprises particles bound by binder; the matrix is porous and non-compressed; the matrix disperses in less than 15 sec in a volume of 15 ml of aqueous fluid; OXC is included in drug-containing particles comprising small particles of OXC and at least one pharmaceutical excipient as carrier; and the content of OXC in the matrix ranges from 35-60% wt based upon the total weight of the matrix.

Some embodiments of the invention include those wherein: a) the at least one surfactant is present in an amount ranging from 0.5-7.0% wt based upon the final weight of the dosage form; b) the at least one sweetener is present in an amount range from 0.01-2.0% based upon the final weight of the dosage form; c) the at least one binder is present in an amount range from 5-15% based upon the final weight of the dosage form; d) the at least one disintegrant is present in an amount range from 10-30% based upon the final weight of the dosage form; and/or e) the at least one glidant is present in an amount range from 0-2% based upon the final weight of the dosage form.

Some embodiments of the invention include those wherein: a) the hardness of the matrix ranges from about 1 to about 7 kiloponds (kp), about 1 to about 3 kp; b) the matrix disperses in 10 sec or less when placed in 15 ml of water or in saliva; c) binder is introduced into the matrix by way of printing fluid used to form the matrix; d) binder is introduced into the matrix by way of bulk powder used to form the matrix; e) the matrix comprises about 150 mg to about 600 mg of OXC; f) the matrix comprises 10 to 40 printed incremental layers; g) the thickness (height) of an incremental layer ranges from 0.006 to 0.014 inches or 0.008 to 0.012 inches; h) the matrix is porous and non-compressed.

The drug-containing particles comprise OXC and at least one, at least two, at least three, at least four, or at least five pharmaceutical excipients. In some embodiments, the drug-containing particles comprise OXC, at least one binder, at least one surfactant, and at least one disintegrant. The drug-containing particles may further comprise sweetener and/or flavorant. In some embodiments, the drug-containing particles comprise OXC, at least two binders, at least one surfactant, and at least one disintegrant.

Some embodiments of the invention include those wherein: a) content of drug-containing particles in the matrix generally ranges from 55-85% wt, 60-80% wt or 65-70% wt based upon the total weight of matrix in the final dosage form; b) the drug-containing particles comprise disintegrant, binder, surfactant and native particles of OXC; c) the content of native particles of OXC in the drug-containing particles ranges from 55-85% wt, 60-80% wt or 65-70% wt, based upon the final weight of the drug-containing particles; d) the content of disintegrant in the drug-containing particles ranges from 0-30%, 1-15%, or 2-5% wt, based upon the final weight of the drug-containing particles; e) the content of binder in the drug-containing particles ranges from 0-10%, 1-7%, or 2-5% wt, based upon the final weight of the drug-containing particles; 0 the content of surfactant in the drug-containing particles ranges from 0-10%, 1-5%, or 1.4-4.2% wt, based upon the final weight of the drug-containing particles; g) the drug-containing particles are manufactured by wet granulation.

The drug-containing particles have an average, mean or median particle size in the range of about 50 to about 400 microns, about 50 to about 300 microns, about 50 to about 250 microns, about 60 to about 250 microns, about 60 to about 100 microns, or about 75 to about 250 microns.

In some embodiments, OXC native particles have an average, mean or median particle size in the range of about 1 to about 90 microns, about 1 to about 75 microns, about 1 to about 50 microns, about 1 to about 30 microns, about 1 to about 15 microns, about 1 to about 10 microns, about 2 to about 14 microns, about 10 to about 80 microns, about 20 to about 70 microns, about 20 to about 60 microns or about 30 to about 50 microns. In some embodiments, OXC natives particles have a particle size distribution with a Dv90 of less than about 100 microns, a Dv90 of less than about 90 microns, a Dv90 of less than about 75 microns, a Dv90 of less than about 50 microns, and/or have a Dv50 of less than about 75 microns, a Dv50 of less than about 50 microns, a Dv50 of less than about 40 microns, a Dv50 of less than about 30 microns, a Dv50 of less than about 20 microns, a Dv50 of less than about 10 microns, a Dv50 of less than about 5 microns, a Dv50 of about 1 to about 40 microns, a Dv50 of about 1 to about 30 microns, a Dv50 of about 1 to about 20 microns, a Dv50 of about 5 to about 15 microns and/or have a Dv10 of less than about 30 microns, a Dv10 of less than about 20 microns, a Dv10 of less than about 10 microns, a Dv10 of less than about 5 microns, a Dv10 of less than about 1 microns. All combinations of these Dv10, Dv50 and Dv90 values and ranges are contemplated. The native particle size distribution and/or effective particle size distribution can be mono-modal, bi-modal or multi-modal. OXC can be present as a mixture of two or more different native drug powders each having its own native particle size distribution and/or method of preparation. The drug-containing particles can be present as a mixture of two or more different powders each having its own effective particle size distribution and/or method of preparation. In some embodiments, the OXC comprises a milled first form and a micronized second form. The amount of first form can range from 0-25% wt, 10-15% wt or 13-15% wt, and the amount of second form can range 100-75% wt, 90-85% wt, or 97-85% wt, respectively.

Some embodiments of the invention include those wherein the matrix comprises about 150 to about 1200 mg, about 150 mg, about 300 mg, about 450 mg, about 600 mg, about 750 mg, about 900 mg, about 1050 mg or about 1200 of OXC.

The matrix rapidly disperses (disintegrates) in a small amount of aqueous fluid. Some embodiments of the invention include those wherein the matrix disperses in about 30 sec or less, about 20 sec or less, about 15 sec or less, about 10 sec or less, or about 5 sec or less when placed in a small amount of aqueous fluid. In some embodiments, the disintegration time is determined according to USP <701>.

A method of treating a disease or disorder that is therapeutically responsive to OXC is provided. The method comprises daily administration of one, two or three dosage forms of the invention to a subject in need thereof over a treatment period lasting days, weeks or months thereby reducing or eliminating one or more symptoms of the disease or disorder. In some embodiments, a 3DP dosage form comprising a dose of about 150 to about 1200 mg, or about 150 to about 600 mg is administered twice daily for a treatment period.

A method of preparing an orodispersible dosage form is also provided. The method comprises forming a non-compressed porous matrix as described herein by forming incremental layers of powders and depositing printing fluid on each incremental layer to bind disintegrant, binder, surfactant, glidant, sweetener and drug-containing particles of OXC into a rapidly orodispersible non-compressed porous matrix.

The invention includes all combinations of the aspects, embodiments and sub-embodiments disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

DETAILED DESCRIPTION OF THE INVENTION

Figure 1:
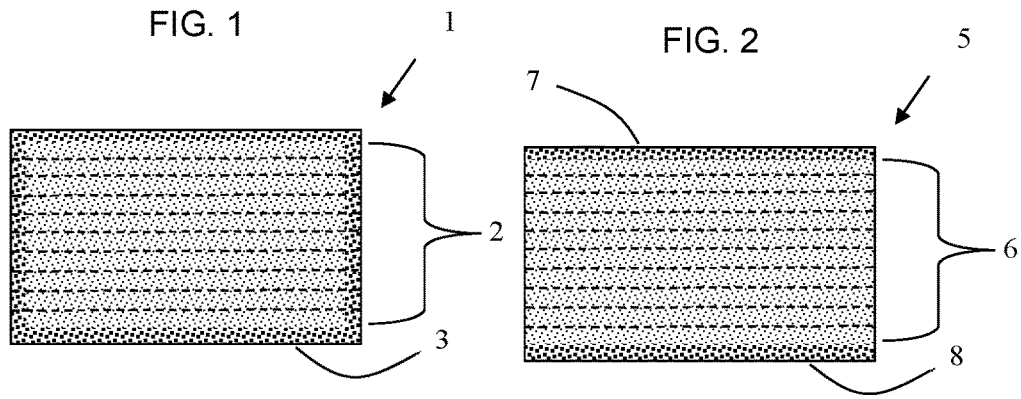
FIG. 1 depicts a sectional front elevation of an orodispersible dosage form made from a three-dimensionally printed matrix comprising sequentially-formed incremental layers of bound bulk material.

As used herein and unless otherwise specified, the term oxcarbazepine (OXC) refers to the drug in underivatized (10,11-Dihydro-10-oxo-5H-dibenz[b,f]azepine-5-carboxamide) or derivatized form. Oxcarbazepine is available from Jubilant Life Sciences (Nanjangug, Mysore, Karnataka, India), CTX Life Sciences Pvt. Ltd. (Sachin, Surat, Gujarat, India), Trifarma S.p.A (Milano, Italy) and Fabrica Italiana Sintetici S.p.A (Montecchio Maggiore-Vicenza, Italy). OXC can be present in crystalline or amorphous form. Polymorphs of oxcarbazepine have been recognized recently (e.g., in J. Pharm Sci 99 (2) 2010:794-803) and are considered to be within the scope of the term oxcarbazepine.

As used herein, "native particles" refers to particles of a compound without any other added components, i.e. native particles of OXC are particles containing OXC, wherein the particles do not contain any added excipient(s). "Drug-containing particles" refers to preformed particles comprising "native particles of OXC" and one or more excipients.

The drug-containing particles are necessarily larger in size than the native particles. The drug containing particles can be granules, beads, pellets, or other engineered particles or agglomerates that otherwise incorporate the smaller, primary drug particles themselves and can withstand conventional powder handling for flow and transfer.

As used herein and unless otherwise specified, "particle size" and "actual particle size" refer to the particle size of a compound without any other added component(s), i.e. the particle size of the native particles of OXC, or refers to the particle size of the drug-containing particles.

The present invention provides a rapidly orodispersible dosage form comprising drug-containing particles comprising OXC and one or more pharmaceutical excipients. The dosage form comprises a non-compressed matrix of particles bound by binder. The matrix comprises the drug-containing particles, disintegrant, binder, surfactant, glidant, sweetener and glycerin. The matrix is porous and disperses within less than 20 sec when placed in a small amount of water.

The impact of particle size of OXC upon characteristics of a 3DP orodispersible dosage form was evaluated by directly blending OXC with other excipients to form the powder material used for printing. It was determined that lots with very small particle size, e.g. mean particle size>10 microns, produced dosage forms with unacceptably rough surfaces and poor (unacceptably low) hardness. Lots with large mean particle size, e.g. 40-50 microns, produced better surface texture and hardness; however, those particles are substantially larger than desired for oral administration.

Inventive drug-containing particles of OXC were prepared using small particle size OXC, disintegrant, binder, and glidant. The inventive particles were prepared by wet granulation according to Example 1. Wet granulation can be conducted in a low shear mixer, e.g. planetary mixer, or high shear mixer, e.g. GMX mixer. Comparator drug-containing particles were prepared by dry granulation with roller compaction.

The ratio of effective particle size to native drug particle size will vary according to the respective mean, median, average or D50 particle size distributions: the smaller the native particle size and the larger the effective particle size, then the larger the ratio, and vice versa. For example, if the average native particle size is such that 90%-100% of the drug is <10 microns, then the ratio of effective particle size to native particle size might be in the range of 10:1 to 200:1. Likewise, if the average native particle size is such that NMT 20% of the drug is <32 microns, 40-70% of the drug is <63 microns, 70-95% of the drug is <125 microns, and 100% o the drug is <250 microns, then the ratio of effective particle size to native particle size might be in the range of >1:1 to about 10:1. Accordingly, the ratio can be in the range of >1:1 to about 200:1, or 2:1 to 100:1, or 3:1 to 50:1. Use of more than one grade of native drug is contemplated, which may comprise one or more native particle size distributions. In some embodiments having more than one grade of native drug, more than one ratio of effective particle size to native drug particle size may be used to describe the relative particle sizes. In some embodiments, there is a first ratio of effective particle size to native particle size of >1:1 to 5:1 with respect to a first native API, and a second ratio of effective particle size to native particle size of 20:1 to 50:1 with respect to a second native API.

Then, three-dimensionally printed (3DP) dosage forms comprising the various different drug-containing particles of OXC were prepared according to Example 3. The resulting 3DP dosage forms were evaluated for hardness, dispersion time and friability to determine which of the drug-containing particles provided suitable 3DP orodispersible dosage forms with very rapid dispersion times, adequate hardness and minimal friability. It was determined that only the drug-containing particles made by wet granulation, preferably high shear wet granulation, provided 3DP dosage forms meeting these stringent performance criteria. None of the comparator formulations made by dry granulation provided 3DP dosage forms meeting these stringent performance criteria. This finding is quite unexpected, since the compositions of the comparator drug-containing particles were the same as those of the inventive drug-containing particles The weight ratio of OXC to other excipients in the drug-containing particles can be varied; however, doing so will have an impact upon hardness, dispersion time, friability, dosage form size and dose of drug in the dosage form. If the excipient content in the drug-containing particles is too low, performance of the dosage form is sacrificed. If excipient content in the drug-containing particles is too high, the dosage form size has to be increased substantially in order to include a suitable dose of OXC therein, thereby making it extremely difficult to prepare reasonably sized dosage forms containing high amounts of OXC.

Drug-containing particles, especially granules prepared by wet granulation, can be used to prepare rapidly dispersible 3DP matrices comprising OXC having a hardness in the range of 1-3 kP and a dispersion time in water of 15 sec or less, or 10 sec or less. Suitable drug-containing particles comprise 65-70% wt OXC, 21.5-23% wt diluent/disintegrant, e.g. microcrystalline cellulose, 3-5% wt superdisintegrant, e.g. croscarmellose, 1-4.5% wt surfactant, e.g. sodium lauryl sulfate, and 2.5-5% binder, e.g. hydroxypropylcellulose. Drug-containing particles produced by high shear wet granulation had a Dv0.5 of about 60-100 microns.

It has been determined that inclusion of a surfactant in the printing fluid, bulk powder and drug-containing particles aids in ensuring rapid dispersion of the 3DP dosage form when placed in a minimal amount of water. The surfactant serves to enhance wetting of the particles. The surfactant need only be present in an amount sufficient to enhance dispersion as compared to another 3DP dosage form excluding the surfactant. If the surfactant is present in too high of an amount, however, it will negatively impact mouth feel, performance and/or physical properties of the dosage form. The surfactant can be included in the drug-containing granule, bulk powder and/or printing fluid. In some embodiments, the total amount of surfactant present in the drug-containing particles ranges from about 0-5%, >0-5%, 1-4.2%, 2-3% wt. based upon the weight to the drug-containing particles. In some embodiments, the amount of surfactant present in the bulk powder, excluding the drug-containing particles, ranges from about 0-5%, >0-5%, 1-4.2%, 2-3% wt. based upon the weight to the bulk powder.

The rapidly dispersible dosage form can disperse (disintegrate) in about 30 seconds or less, about 20 seconds or less, about 15 seconds or less, about 10 seconds or less, about 5 sec or less, about 4 sec or less, or about 3.5 sec or less when placed in a small volume of aqueous fluid, such as a saliva, gastric fluid and/or a sip of water. In some embodiments, the dispersion (disintegration) time is measured in a small volume of 20 ml or less, 15 ml or less, 10 ml or less, 5 ml or less, 3 ml or less and at least 1 ml of an aqueous fluid. In some embodiments, the disintegration time is determined according to USP <701>.

The small volume of aqueous fluid can be a sip such as a volume 50 ml or less, 40 ml or less, 30 ml or less, 20 ml or less, 10 ml or less, 5 ml or less, 2.5 ml or less or 1 ml or less. The small volume can be at least 0.1 ml, at least 0.25 ml, at least 0.5 ml, at least 0.75 ml, at least 1 ml, at least 1.5 ml or at least 2 ml. All possible combinations of these volumes are contemplated. Suitable ranges for the small volume include 0.1 to 50 ml, 0.1 to 40 ml, 0.1 to 30 ml, 0.1 to 20 ml, 0.1 to 10 ml, 0.2 to 10 ml, 0.3 to 10 ml, 0.5 to 10 ml, 1 to 10 ml, 5 to 10 ml, 1 to 7.5 ml, 1 to 5 ml, 0.5 to 3 ml, or other such ranges. Preferably, the sip is about 15 ml (one tablespoon) of water. Preferably a sip is about 2 to about 30 ml, about 10 to about 15 ml (1 tablespoon) or about 13 ml of water (fluid).

In some embodiments, the dosage form comprises not more than 10% wt., not more than 7.5% wt., not more than 5% wt., not more than 4% wt., not more than 3% wt., not more than 2.5% wt., not more than 2% wt. or not more than 1.5% wt. moisture as determined by loss on drying (LOD) at 120° C. In some embodiments, the dosage form comprises at least 0.1% wt., at least 0.2% wt., at least 0.5% wt., at least 0.75% wt., at least 1% wt., at least 1.5% wt., at least 2% wt., at least 2.5% wt., at least 3% wt., at least 4% wt., or at least 5% wt. moisture as determined by loss on drying at 120° C. In some embodiments, the dosage form comprises 0.1 to 10% wt, 0.2 to 7.5% wt, 0.25 to 5% wt, 0.5 to 4% wt or 0.75-2% wt moisture. All combinations of these various limits are within the scope of the invention.

In some embodiments, the overall hardness (as determined by a tablet breaking force assay according to USP <127>) of the matrix ranges from about 0.5 kiloponds (kp) to about 5 kp or from about 1 kp to about 3 kP. In some embodiments, the overall hardness is at least 1.0 kp, at least 1.5 kp or at least 2 kp. In some embodiments, the overall hardness is no more than 5 kp, no more than 4 kp or no more than 3 kp.

The term friability is the tendency of the matrix to lose material from its outer edges and surfaces upon mechanical insult. Friability is reduced by increasing the hardness. In some embodiments, the dosage form possesses a friability of less than about 25%, preferably less than about 10% as determined according to USP <1216> and as further described below.

In some embodiments, the porosity of the matrix ranges from about 10% to about 90% or from about 30% to about 70% of the dosage form volume.

In some embodiments, the bulk density of the matrix (as determined by measurement of weight and dimensions and calculation) ranges from 150 (mg/mL) to about 1300 (mg/mL), 200-1000 (mg/ml), or from about 300 (mg/mL) to about 700 (mg/mL).

The rapidly dispersible dosage form of the invention is made by a three-dimensional printing (3DP) process. Suitable equipment assemblies for three-dimensional printing of articles are commercially available or are already in use: Massachusetts Institute of Technology Three-Dimensional Printing Laboratory (Cambridge, Mass.), Z Corporation's 3DP and HD3DP™ systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' Invision™ system (Valencia, Calif.). Other suitable 3DP systems are disclosed in U.S. No. 20080281019, No. 20080277823, No. 20080275181, No. 20080269940, No. 20080269939, No. 20080259434, No. 20080241404, No. 20080231645, No. 20080229961, No. 20080211132, No. 20080192074, No. 20080180509, No. 20080138515, No. 20080124464, No. 20080121172, No. 20080121130, No. 20080118655, No. 20080110395, No. 20080105144, No. 20080068416, No. 20080062214, No. 20080042321, No. 20070289705, No. 20070259010, No. 20070252871, No. 20070195150, No. 20070188549, No. 20070187508, No. 20070182799, No. 20070182782, No. 20060268057, No. 20060268044, No. 20060230970, No. 20060141145, No. 20060127153, No. 20060111807, No. 20060110443, No. 20060099287, No. 20060077241, No. 20060035034, No. 20060030964, No. 20050247216, No. 20050204939, No. 20050179721, No. 20050104241, No. 20050069784, No. 20050061241, No. 20050059757, No. 20040265413, No. 20040262797, No. 20040252174, No. 20040243133, No. 20040225398, No. 20040183796, No. 20040145781, No. 20040145628, No. 20040143359, No. 20040141043, No. 20040141030, No. 20040141025, No. 20040141024, No. 20040118309, No. 20040112523, No. 20040012112, No. 20040005360, No. 20040005182, No. 20040004653, No. 20040004303, No. 20040003741, No. 20040003738, No. 20030198677, No. 20030143268, No. 20020125592, No. 20020114652, No. 20020079601, No. 20020064745, No. 20020033548, No. 20020015728, No. 20010028471, and No. 20010017085; U.S. Pat. Nos. 5,490,962, No. 5,204,055, No. 5,121,329, No. 5,127,037, No. 5,252,264, No. 5,340,656, No. 5,387,380, No. 5,490,882, No. 5,518,680, No. 5,717,599, No. 5,851, 465, No. 5,869,170, No. 5,879,489, No. 5,934,343, No. 5,940,674, No. 6,007,318, No. 6,146,567, No. 6,165,406, No. 6,193,923, No. 6,200,508, No. 6,213,168, No. 6,336, 480, No. 6,363,606, No. 6,375,874, No. 6,508,971, No. 6,530,958, No. 6,547,994, No. 6,596,224, No. 6,772,026, No. 6,850,334, No. 6,905,645, No. 6,945,638, No. 6,989, 115, No. 7,220,380, No. 7,291,002 No. 7,365,129, No. 7,435,368, No. 7,455,804, No. 7,828,022, No. 8,017,055; PCT International Publications No. WO 00/26026, No. WO 98/043762, No. WO 95/034468, No. WO 95/011007; and European Patent No. 1,631,440, which employs a cylindrical (radial or polar) coordinate-based system due to its construction. The entire disclosure of each of these references is hereby incorporated herein.

The 3DP process described herein requires a powder layering system that forms a layer of powder and printing system that applies a printing fluid to the layer of powder according to a predetermined pattern, thereby forming an incremental printed layer. The printing fluid serves to form bound particles of powder, i.e. particles that are adhered to one another by one or more pharmaceutical excipients and/or one or more active ingredients. Incremental printed layers are formed one on top of another to vertically build the dosage form of the invention, thereby forming a dosage form comprising plural incremental printed layers. The process of spreading powder and depositing droplets is repeated until the desired number of layers for the dosage form is complete. The incremental layers adhere to one another due to bleeding of printing fluid from one layer to an adjacent other layer such that one or more excipients and/or one or more active ingredients adhere to both adjacent layers. Following completion of the initial three-dimensional structure, residual printing fluid is removed from or reduced in the dosage form by drying. The evaporation of solvent during the drying process leaves a matrix having a three-dimensional architecture comprising the particles of bulk material bound by solidified binder and/or other components including one or more active ingredients and/or any optional pharmaceutically acceptable excipients.

The three-dimensional printing process is normally conducted at ambient temperatures. The process can utilize a variety of printing fluids, including biologically compatible organic and aqueous solvents. The process is additive, whereby microscopic features are incorporated layer by layer, allowing a wide range of possible architectures to be constructed precisely on a sub-millimeter scale. Using three-dimensional printing to control simultaneously both the microscopic features and the macroscopic shape, the unique drug delivery systems of the present invention are obtained.

A particularly suitable printing assembly for three-dimensional printing of the instant dosage form is described in U.S. application No. 61/696,839, filed Sep. 5, 2012, the disclosure of which is hereby incorporated by reference in its entirety. The assembly includes build modules each having an incrementally height adjustable platform disposed within a cavity of the build modules, a powder layering system, a printing system, a printing fluid removal system and a dosage form handling system.

In general, at least two components are used in the three-dimensional printing process used to prepare the matrix of the rapidly dispersing dosage forms. The first component is the powder material to be included in the incremental powder layers. The second component is the printing fluid (in some cases the fluid may also contain a binder) that is dispensed by a printhead onto the powder layer. In some embodiments, the powder material is comprised of bulk powder comprising plural excipients and of drug-containing particles comprising OXC and plural excipients. The excipients in the bulk powder can be the same as or different than the excipients in the drug-containing particles. In some embodiments, one or more excipients in the bulk powder is different that one or more excipients in the drug-containing particles.

At least one component of the matrix must serve as a "binding agent" that binds particles of bulk powder together in the completed three-dimensional matrix. The binding agent produces adhesion between particles of the bulk powder and drug-containing particles. It is this adhesion that enables the dosage form to maintain a fixed shaped (geometry) and maintain its characteristics of hardness and friability adequate to permit handling and storage. The strength and extent of the binding depends on the proportion of the binding agent either in the powder layer or dissolved in the solvent, and is a function of the amount of fluid deposited. The term adhesion means the bonding or binding of particles of the bulk material to each other or to particles of another material present. There are various ways in which a binding agent can be included in the matrix. The invention contemplates a combination of one or of two or more of these different ways.

In some embodiments of the method of preparation of the matrix, binding agent is present in the bulk powder, the drug-containing particles, the printing fluid, or a combination or two or three thereof. A binding agent in the printing fluid can be the same as or different than a binding agent in the bulk powder and/or drug-containing particles.

The binding agent can be a pharmaceutically acceptable binder. Including a pharmaceutical "binder" as the binding agent in the printing fluid will result in a different internal microstructure of the dosage forms, particularly the pore size, than the internal microstructure of an otherwise same dosage form excluding binder in the binding solution. Upon printing, as the solvent evaporates, binder remains as a solid residue, which occupies void space in between powder particles, e.g. particles of disintegrant or drug. The resulting structure will have higher density compared to tablets fabricated without binder in the printing fluid.

The invention provides a process for the preparation of a rapidly dispersing solid dosage form comprising a three-dimensionally printed solid porous matrix comprising a bulk powder, binder and drug-containing particles of OXC, the process comprising: (a) providing a powdered mixture of one or more disintegrants, one or more binders, one or more sweeteners, one or more humectants, one or more glidants and drug-containing particles (comprising OXC and one or more excipients), together with any optional pharmaceutically acceptable excipients; (b) forming an incremental layer of the powdered mixture; (c) applying to the incremental layer droplets of printing fluid according to a predetermined pattern to form a printed incremental layer; (d) repeating (b) and (c) a predetermined number of times, thereby providing a three-dimensionally printed moist matrix; and (e) removing or reducing the amount of printing fluid in the moist matrix, thereby providing three-dimensionally printed solid porous matrix having a composition, moisture content, porosity, overall bulk density, hardness, matrix dispersion time, in vitro drug dissolution time, in vitro dispersion behavior, in vivo pharmacokinetic behavior, structure, incremental layer thickness, drug particle size, drug-containing particle size, disintegrant particle size, drug content, and/or friability within the ranges specified herein.

The dosage form of the present invention may be further shaped as desired to facilitate placement thereof in the buccal cavity of a subject. One such embodiment may be a wafer-like shape, donut, ring, tube, cube, spheroid, ellipsoid or rectangular box.

FIG. 1 depicts a sectional front elevation of an orodispersible dosage form (1) made from a three-dimensionally printed matrix comprising sequentially-formed incremental layers of bound bulk material (2-3). The exterior surfaces (3) envelope a middle portion (2). The exterior surfaces have a greater hardness than the interior portion. This dosage form is made by three-dimensionally printed plural incremental layers. The bottom incremental layer, which defines the lower surface, and the upper incremental layer, which defines the upper surface, and the circumferential surfaces (left and right of the middle portion) are harder than the interior portion. The increased hardness is achieved by using a higher saturation level, higher content of binder or as otherwise described herein. The increased hardness at the periphery of the incremental layers of the middle portion is achieved by increasing the saturation level and/or content of binder at the periphery, but not the center (non-peripheral portion) of the respective incremental layers.

Figure 2:
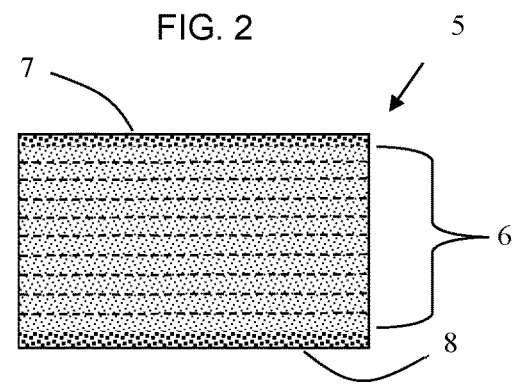
FIG. 2 depicts a sectional front elevation of an alternate embodiment of an orodispersible dosage form made from a three-dimensionally printed matrix.

FIG. 2 depicts a sectional front elevation of an alternate embodiment of an orodispersible dosage form (5) made from a three-dimensionally printed matrix. The bottom incremental layer, which defines the lower surface (8), and the upper incremental layer, which defines the upper surface (7) are harder than the interior portion (6) comprising plural incremental layers. The dosage forms (1) and (5) differ primarily in the process used to print the middle incremental layers, the layers of (6) not having a periphery with increased hardness.

Figure 3A:
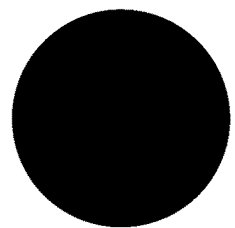
FIGS. 3A-3E depict various different printing patterns that can be used to apply printing fluid to incremental layers of powder.
Figure 3B:
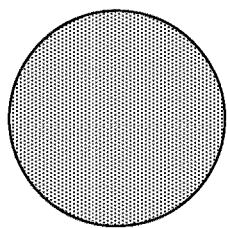
Figure 3C:
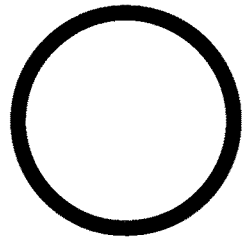
Figure 3D:
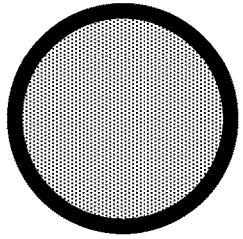
Figure 3E:
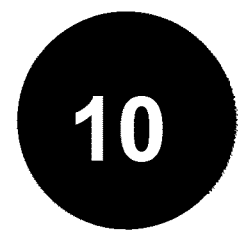

FIGS. 3A-3E depict the top plan view of three different print patterns that can be used to prepare the printed incremental layers of a 3DP orodispersible matrix of the invention. Even though each print pattern is depicted as being circular, substantially any geometry can be used, e.g. circle, oval, square, rectangle, oblong circle, etc. FIG. 3A depicts a first solid print pattern wherein substantially the same full, heavy or higher saturation level is used throughout the entire print area. FIG. 3B depicts a second solid print pattern wherein substantially the same medium, low, light or lower saturation level is used throughout the entire print area. This second solid pattern is referred to as a grayscale pattern since it has a reduced saturation level. FIG. 3C depicts an annular (hollow) print pattern wherein printing fluid is applied to the periphery of the print area but not toward the center of the print area. FIG. 3D depicts a combination annular and grayscale print pattern wherein printing fluid is applied to the periphery of the print area at a higher saturation level and toward the center of the print area at a grayscale (reduced) saturation level. FIG. 3E depicts an indicum print pattern wherein substantially the same saturation level is used throughout the entire print area except in the indicum region(s) wherein no printing fluid is applied thereby forming a debossed indicum in the surface of the final dosage form.

In some embodiments, the dosage form comprises (consists essentially of or consists of) the following types of printed incremental layers: a) plural layers of first solid print pattern, and plural layers of combination annular and grayscale print pattern; b) plural layers of first solid print pattern, plural layers of annular print pattern, and plural layers of combination annular and grayscale print pattern; c) plural layers of first solid print pattern, plural layers of annular print pattern, plural layers of combination annular and grayscale print pattern, and plural layers of indicum print pattern; d) plural layers of first solid print pattern, plural layers of annular print pattern, plural layers of combination annular and grayscale print pattern, plural layers of first solid print pattern, and plural layers of indicum print pattern; e) plural layers of first solid print pattern, plural layers of grayscale print pattern, and plural layers of first solid print pattern; f) plural layers of grayscale print pattern; g) plural layers of combination annular and grayscale print pattern; h) plural layers of first solid print pattern; i) plural layers of first solid print pattern and plural layers of annular print pattern; or j) plural layers of first solid print pattern, plural layers of combination annular and grayscale print pattern, and plural layers of indicum print pattern.

In some embodiments, the dosage form comprises (consists essentially of or consists of) the following types of incremental layers grouped into respective sections of the dosage form: a) a first end comprising plural layers of first solid print pattern; a middle portion comprising plural layers of annular print pattern and plural layers of combination annular and grayscale print pattern; and a second end comprising plural layers of indicum print pattern; b) a first end comprising plural layers of first solid print pattern; a middle portion comprising plural layers of combination annular and grayscale print pattern; and a second end comprising plural layers of first solid print pattern and/or plural layers of indicum print pattern; c) a first end comprising plural layers of first solid print pattern; a middle portion comprising plural layers of annular print pattern, plural layers of combination annular and grayscale print pattern; and a second end comprising plural layers of first solid print pattern and/or plural layers of indicum print pattern; or d) a first end comprising plural layers of first solid print pattern; a middle portion comprising alternating groups of layers, wherein one group comprises plural layers of annular print pattern, and another group comprises plural layers of combination annular and grayscale print pattern; and a second end comprising plural layers of first solid print pattern and/or plural layers of indicum print pattern.

Figure 4A:
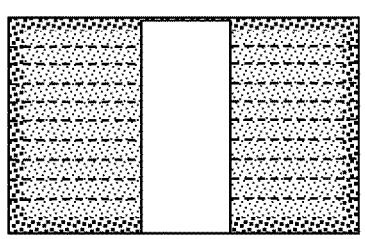
FIG. 4A depicts a sectional front elevation of an alternate embodiment of an orodispersible dosage form made from a three-dimensionally printed matrix.
Figure 4B:
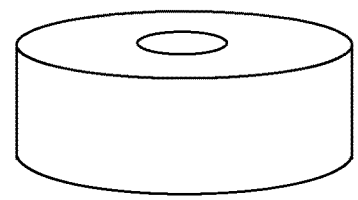
FIG. 4B depicts a perspective view of the dosage form of FIG. 4A.

The dosage form can also be shaped as a donut, ring or tube. FIG. 4A depicts an exemplary dosage form wherein the core of the dosage form about the vertical axis of the cylindrical shape has been left out or removed during manufacture of the dosage form. The diameter of the bore or hole can be in the range of 3-10 mm. In some embodiments, the hole is created via an unprinted zone within the dosage form and reaching at least one exterior surface such that unbound powder empties out. FIG. 4B depicts a perspective view of the dosage form of FIG. 4A.

The physical properties of the dosage form can be controlled by varying incremental powder layer thickness, powder composition, printing fluid composition, printing fluid saturation level (print density) on a layer, and identity and amount of the excipients included within the dosage form, e.g. identity and amount of disintegrant, binder, sweetener, surfactant. These variables exhibit different levels of effect upon dosage form hardness, bulk density, disintegration time, dissolution time, bioavailability, moisture content, taste, and friability. It was determined that the result effective variables include, at least, the amount of drug, amount of disintegrant, amount of binder, layer thickness, identity of some components, and composition of the drug-containing particles.

Three-dimensional printing can have spatial descriptors in each of three different, typically orthogonal directions. In three-dimensional printing, fluid may be deposited in drops or in fluid units resembling drops. Drops may be deposited in a succession that forms a line corresponding to the motion of the printhead. The spacing between those drops is the drop-to-drop spacing. After completion of one line, another line may be deposited adjacent to the earlier-deposited line and separated from the earlier-deposited line by a distance that is a line-to-line spacing. After completion of printing on a layer of powder, another powder layer may be deposited, with each powder layer having a layer thickness. The powder layer thickness is the third descriptor.

In some instances, the spacing of droplets may be described in terms of the resolution of the printing system, often expressed as dots per inch (dpi), which is the reciprocal of droplet spacing. For example, resolutions of 300 and 600 dpi correspond to droplet spacing's of about 84.7 microns and about 42.3 microns, respectively. The drop-to-drop spacing (within a line), or the line spacing (spacing of droplets from one line to the next), or any other spacing of droplets may be described in terms of resolution expressed in dpi. In some instances, layer-by-layer instructions for making the dosage forms may consist of a series of pixelated images characterized by a resolution in dots-per-inch in each of two orthogonal linear directions. In some instances, these pixelated images are 1-bit monochrome images, alternately referred to as binary or bi-level images in which each pixel contains one bit of information (0 or 1) that may be represented as either black or white onscreen.

In some instances, the relative amount of binding in localized regions of the dosage form is achieved by "grayscaling" (i.e., use of a grayscale print pattern) in the dosage form design. In the case of 1-bit monochrome images used for machine instructions, grayscaling is achieved by changing the number of "black" pixels relative to "white" pixels in a chosen region of a dosage form, or in a chosen layer of a dosage form, or throughout a dosage form. Any other regions that may be "solid" by using all black pixels. In some embodiments, the dosage form design includes a "solid" exterior and a "grayscaled" interior. In some embodiments, grayscaling may be achieved with equally spaced black pixels amongst white pixels to reach an overall ratio of black to white pixels in the grayscaled region. In other embodiments, grayscaling may be achieved with randomly placed black pixels amongst white pixels to achieve an overall ratio of black to white pixels in the grayscaled region. In still other embodiments, grayscaling may be achieved with a chosen pattern (e.g., parallel lines, hashed pattern, dot pattern) of black pixels amongst white pixels to achieve an overall ratio of black to white pixels in the grayscaled region.

In three-dimensional printing, a voxel or unit volume may be defined by one drop-to-drop spacing in the fast axis direction of motion, by one line-to-line spacing in the slow axis direction of motion, and by one layer thickness in the vertical direction. Some of this unit volume is occupied by powder particles, and the remainder of the unit volume is empty space that collectively has a volume that is the void volume.

The saturation level (print density) describes how much of the void space in this unit volume is occupied by liquid which is dispensed in a drop or fluid unit which is dedicated to that particular voxel. The saturation level is the ratio of the dispensed fluid volume to the volume of empty space in the voxel. In general, in three-dimensional printing, saturation levels may be chosen to be slightly less than, or somewhere approximately equal to, 1.0, also expressed as 100%. Excessively low saturation levels tend to result in poor structural integrity. Excessively high saturations levels tend to result in excessive bleeding of liquid beyond where the liquid was deposited. In the present dosage form, the saturation level during the step of applying printing fluid to a powder layer ranges from about 85% to about 120%, about 10% to about 110%, about 15% to about 80%, about 20% to about 50% or about 15% to about 35% in aggregate across the dosage form, or otherwise in selected regions of the dosage form.

Suitable printing devices include those having a continuous jet printhead or those having a drop-on-demand printhead. A continuous jet printhead provides a continuous jet (spray) of droplets while depositing printing fluid onto a powder layer. A drop-on-demand printhead only deposits droplets of printing fluid onto the powder layer if it receives an instruction (demand, operational command) to do so. A printhead scans (applies fluid to) the surface of powder layer from left to right at a predetermined rate, e.g. a scan rate, to form a line of droplets. A high scan rate will result in a lower saturation level, and a low scan rate with result in a higher saturation level when comparing printing fluid deposition at a constant volume per unit time. When considering the situation where binder is present in the binding solution, an increase in the print speed from 1.0 m/s to 2.0 m/s reduces the total volume of binder solution deposited in the tablets by half. As the print speed increases, the bulk density (theoretical, calculated from the weight and dimensions of the tablet) decreases. A simultaneous decrease in the dimensions and weight of the tablets is also seen. This decrease is attributed to the fact that a decrease in the total volume of binder droplets deposited onto the powder results in a decrease in the extent of binder solution spreading in the powder. As expected, increasing the print speed also decreases the flash time and the hardness and increases the friability of the tablets. This result is obtained because the proportion of binder decreases in the tablets as the print speed increases. An increase in the print speed also increases the void volume inside the tablets, as illustrated by an increase in the percent volume of the tablets penetrated by mercury at 30 psi (% intrusion).

When using a continuous jet printhead, the printhead scans at a rate of about 0.5 to 3.0 m/sec, and most preferably at about 1.75 m/sec. When using a drop-on-demand jet printhead, the printhead scans at a rate of 0.1 to 1 m/sec, most preferably at about 0.5 m/sec.

The volume of individual droplets can be varied as desired. Increasing the volume of the droplet increases the saturation level and decreasing the volume of a droplet decreases the saturation level when comparing printing fluid deposition at a constant scan rate. When using a continuous jet printhead, the size of the fluid droplets delivered by the printhead preferably ranges from about 15 µm to about 150 µm in diameter. When using a drop-on-demand printhead, the size of the fluid droplets delivered by the printhead preferably ranges from about 50 µm to about 500 µm in diameter.

The flow rate of the fluid delivered by the printhead can be varied as desired. Increasing the flow rate will increases the saturation level and decreasing the flow rate decreases the saturation level when comparing printing fluid deposition at a constant scan rate. As discussed herein, the printhead deposits droplets of printing fluid to form parallel lines thereof in the powder layer. When using a continuous jet printhead, the line spacing ranges from about 20 to about 1000 µm, about 50 to about 500 µm, or and preferably about 100 to 200 µm. When using a drop-on-demand jet printhead, the line spacing ranges from about 100 to about 1500 µm, about 250 to about 1000 µm, or preferably are about 500 to 750 µm.

The powder layering system and the height adjustable platform cooperate to form thin incremental layers of powder in the build modules. The total thickness (height) of the dosage form will be a function of the number and thickness of the incremental layers. The number of printed incremental layers typically ranges from 5 to 50. A matrix will typically comprise (consist essentially of or consist of) 20 to 50, 20 to 40, 30 to 40 or 30 to 35 printed incremental layers. The "end" section of a dosage form will typically comprise 1 to 10, 1 to 7, 2 to 7, or 4 to 6 printed incremental layers. An end section with an indicum will typically comprise 2 to 10, 2 to 7, or 4 to 7 printed incremental layers. The balance of the printed incremental layers will comprise the middle portion, with respect to the vertical height, of the dosage form. The middle portion will typically comprise 5 to 40, 10 to 30, 10 to 20, or 20 to 30 printed incremental layers.

The incremental layers are of a predetermined height (vertical thickness), which typically varies from 0.005 to 0.015 inches, 0.008 to 0.012 inches, 0.009 to 0.011 inches, 100-300 µm, 100-500 µm, about 200 µm, about 250 µm inches. As thicker incremental layers are used, an increasing amount of printing fluid must be deposited on that layer to ensure adequate binding both within the plane of the layer and layer-to-layer. Conversely, for a thinner incremental layer a lesser amount of printing fluid must be deposited to obtain the same extent of binding. For a given amount of printing fluid deposited per layer, using a larger layer thickness will reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to handle at all. In some embodiments, the thickness of the incremental layers ranges from 100-400 microns, 150-300 microns, or 200-250 microns. In one preferred embodiment, the layer thickness is 200 microns. In another preferred embodiment, the layer thickness is 250 microns.

Dosage forms produced by the 3DP process described herein vary in size according to the content of OXC and the respective drug-containing particles. In order to minimize dosage form size, the content of drug-containing particles should be maximized and the content of OXC in the drug-containing particles should be maximized; however, as described herein, the resulting dosage form must possess sufficient hardness and a very rapid dispersion time. When the content of OXC in the drug-containing particles is in the range of 65-70% wt, and the content of drug-containing particles in the matrix is about 60%, a matrix having a 150 mg dose of OXC can weigh about 380-390 mg, a matrix having a 300 mg dose of OXC can weigh about 770-780 mg, and a matrix having a 600 mg dose can weigh about 1540-1560 mg. Accordingly, if the matrix comprises a higher percentage of drug-containing particles or if drug-containing particles having a higher percentage of OXC are employed, the dosage form weight can be decreased correspondingly and vice versa.

One or more pharmaceutically acceptable excipients can be included in bulk powder material and/or the printing fluid. Each excipient may be independently selected upon each occurrence from a water soluble, aqueous fluid soluble, partially water soluble, partially aqueous fluid soluble, water insoluble or aqueous fluid insoluble excipient as needed to provide the required particle-to-particle binding in a printed matrix.

Most pharmaceutically acceptable excipients, both small molecules and polymers, can be employed, which allow a pharmaceutically active ingredient to be loosely encased in a porous structure (a matrix of bound particles) that is subject to rapid dispersion in the presence of an appropriate aqueous fluid, e.g., saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

Suitable types of excipients for the dosage form include binder, disintegrant, dispersant, sweetener, glidant, flavorant, surfactant, humectant, preservative and diluent. Although conventional pharmaceutical excipients may be used, they may not always function in precisely the same manner as with traditional pharmaceutical processing One or more binders can be included in the printed matrix. The binder may be included in either the bulk powder, drug-containing particles and/or in the printing fluid dispensed through the printhead. The binder is independently selected upon each occurrence. Adhesion of the particles to and/or by the binder occurs either when the binder is contacted by the printing fluid from the printhead or when it is present (i.e., soluble) in the printing fluid. The binder is preferably water soluble, aqueous fluid soluble, partially water soluble or partially aqueous fluid soluble. In some embodiments, the printing fluid comprises 0-10% wt of binder. In some embodiments, the bulk powder comprises >0 to 50% wt, 10% to 45%, 20% to 45%, 25-40%, 25-35% wt of binder. In some embodiments, the drug-containing particles comprise >0 to 10%, 2 to 10%, 2 to 7%, or 2 to 5% wt of binder. In some embodiments, the printed matrix comprises >0 to 50% wt, 10% to 45%, 20% to 45%, 25-40% wt of binder. In some embodiments, binder is absent from the printing fluid or absent from the bulk material.

Suitable binders include water-soluble synthetic polymer, carboxymethylcellulose, hydroxypropylcellulose, polyvinlypyrrolidone, hydroxypropyl-methylcellulose, sorbitol, mannitiol, xylitol, lactitol, erythritol, pregelatinized starch, modified starch, arabinogalactan. Preferred binders include polyvinylpyrrolidone (povidone), mannitol, hydroxypropylcellulose, or a combination thereof.

The following materials are considered binders, even though they exhibit low strength binding: spray dried lactose, fructose, sucrose, dextrose, sorbitol, mannitol, xylitol, etc.

One or more disintegrants can be included in the printed matrix. The disintegrant can be present in the bulk powder and/or drug-containing particles. The disintegrant is independently selected upon each occurrence. In some embodiments, the bulk powder comprises 3-20% wt, 3-15% wt, 4-12% wt or 10-16% wt of disintegrant. In some embodiments, the drug-containing particles comprise 15-35% wt, 20-30% or 25-30%% wt of disintegrant.

Suitable disintegrants include microcrystalline cellulose (MCC), croscarmellose (cross-linked carboxymethylcellulose), powdered cellulose or a combination thereof. Preferred disintegrants include microcrystalline cellulose, e.g. AVICEL® PH 101, a combination of two grades of microcrystalline cellulose, and croscarmellose. Suitable grades of AVICEL® are summarized in the table below. The dosage form can comprise one or a combination of the specified grades. All such embodiments containing single grades or a combination of grades are contemplated.

| Product Grades | Nominal Particle Size, μm | Moisture, % | LooseBulk Density, g/cc |
|---|---|---|---|
| Avicel DG | 45 | NMT 5.0 | 0.25-0.40 |
| Avicel PH-101 | 50 | 3.0 to 5.0 | 0.26-0.31 |
| Avicel PH-102 | 100 | 3.0 to 5.0 | 0.28-0.33 |
| Avicel HFE*-102 | 100 | NMT 5.0 | 0.28-0.33 |
| Avicel PH-102 SCG** | 150 | 3.0 to 5.0 | 0.28-0.34 |
| Avicel PH-105 | 20 | NMT 5.0 | 0.20-0.30 |
| Avicel PH-102 SCG | 150 | 3.0 to 5.0 | 0.28-0.34 |
| Avicel PH-200 | 180 | 2.0 to 5.0 | 0.29-0.36 |
| Avicel PH-301 | 50 | 3.0 to 5.0 | 0.34-0.45 |
| Avicel PH-302 | 100 | 3.0 to 5.0 | 0.35-0.46 |
| Avicel PH-103 | 50 | NMT 3 | 0.26-0.31 |
| Avicel PH-113 | 50 | NMT 2 | 0.27-0.34 |
| Avicel PH-112 | 100 | NMT 1.5 | 0.28-0.34 |
| Avicel PH-200 LM | 180 | NMT 1.5 | 0.30-0.38 |
| Avicel CE-15 | 75 | NMT 8 | N/A |

NMT means "not more than".

The binder and disintegrant are key ingredients for controlling the hardness, friability and dispersion time of the matrix. The greater the amount of binder, the higher the hardness, the lower the friability and the slower the dispersion time. On the other hand, increasing the amount of disintegrant provides lower hardness, increased friability and a faster dispersion time. Accordingly, the matrix of the invention comprises a balanced amount of binder and disintegrant.

One or more sweeteners can be included in the printed matrix. The sweetener can be present in the bulk powder, drug-containing particles and/or the printing fluid. Better taste-masking is observed when at least one sweetener is present in at least the printing fluid. The sweetener is independently selected upon each occurrence. The printing fluid, drug-containing particles and/or the bulk powder can have at least one sweetener in common. In some embodiments, the bulk powder comprises >0 to 5% wt, or >0 to 2% wt, or >0 to 1.5% wt of sweetener. In some embodiments, the printing fluid comprises >0 to 5% wt, >0 to 4% wt, >0 to 3% wt, >0 to 2% wt., 0.1 to 5% wt, 0.1 to 4% wt, 0.1 to 3% wt, 0.1 to 2% wt, 0.5 to 3% wt, or 1 to 3% wt sweetener. In some embodiments, the drug-containing particles comprise 0-5% wt of sweetener.

Suitable sweeteners are selected from the group consisting of glycyrrhizinic acid derivative, e.g. magnasweet (monoammonium glycyrrhizinate), sucralose and a combination thereof. The preferred sweetener in the printing fluid is sucralose. Sweetener is present in at least the printing fluid but may also be present in the bulk powder.

One or more flavorants can be included in the matrix. The flavorant can be present in the bulk powder, drug-containing particles, and/or the printing fluid. The flavorant is preferably water soluble, aqueous fluid soluble, partially water soluble or partially aqueous fluid soluble. If present in the bulk powder, the flavorant is preferably present in a form applied to a carrier powder before preparation of the bulk powder. Suitable carrier powders may include starches, modified starches, celluloses, and other powder capable of absorbing, adsorbing, encasing, or encapsulating the flavorant. In some embodiments, the printing fluid comprises 0-5% % wt, 0.01-1.0% wt or 0.05-0.5% wt of flavorant. In some embodiments, the bulk powder comprises 0.1 to 10% wt, or 1 to 10% wt, 2 to 8% wt, 3-7% wt of flavorant-incorporated carrier powder. In some embodiments, the printed matrix comprises 0-10% wt, 0.01-10% wt of flavorant. In some embodiments, the flavorant is absent from the printing fluid or absent from the bulk material. Suitable flavorants include peppermint, spearmint, mint, vanilla, orange, lemon, citrus, lime, grape, cherry, strawberry, chocolate, coffee or a combination thereof.

One or more surfactants can be included in the printing fluid, drug-containing particles or bulk powder. In some embodiments, the printing fluid comprises 0 to about 10%, >0 to about 7%, or about 1 to about 5% wt of surfactant. In some embodiments, the drug-containing particles comprise 0 to about 10%, >0 to about 7%, or about 1 to about 5% wt of surfactant. In some embodiments, the bulk powder comprises 0 to about 10%, >0 to about 7%, about 1 to about 5% wt of surfactant. Suitable surfactants include sodium lauryl sulfate, polysorbate (PEG-ylated sorbitan (a derivative of sorbitol) esterified with fatty acid) or a combination thereof. Suitable polysorbates include polysorbate 20 (Polyoxyethylene (20) sorbitan monolaurate), polysorbate 40 (Polyoxyethylene (20) sorbitan monopalmitate), polysorbate 60 (Polyoxyethylene (20) sorbitan monostearate), polysorbate 80 (Polyoxyethylene (20) sorbitan monooleate), sodium lauryl sulfate, poloxamer (comprising a central (poly(propylene oxide)) flanked by two chains of (poly(ethylene oxide), e.g. LUTROL), low molecular weight polyethylene glycol (e.g. PEG 400)

Even though the dosage form can be preservative-free, one or more preservatives may optionally be included in the printing fluid or powder blend. Suitable preservatives include antifungal or antimicrobial preservatives such as methylparaben and proprylparaben. In some embodiments, the printing fluid comprises 0.001 to 0.2% preservative.

One or more glidants can be included in the bulk powder and/or drug-containing particles. In some embodiments, the bulk powder comprises 0-5% or >0-2% wt of glidant. In some embodiments, the drug-containing particles comprise 0-5% or >0-2% wt of glidant. Suitable glidants include fumed silica (colloidal silicon dioxide).

The matrix may also comprise glycerin (glycerol) introduced therein either by way of the bulk powder or the printing fluid. Glycerin can exhibit characteristics of a humectant, sweetener, preservative, lubricant, saponifier or solvent. The present inventors have discovered that glycerin unexpectedly behaves contrary to other excipients when included in a three-dimensionally printed dosage form. As noted above, increasing the amount of other excipients disclosed generally results in increased hardness with concomitantly increased disintegration time; however, increasing the amount of glycerin results in increased hardness but unexpectedly reduced disintegration time. The ability of glycerin to behave in this manner is particularly advantageous and has not been observed with any other material incorporated into a three-dimensionally printed orodispersible dosage form.

In some embodiments, glycerin is included in the printing fluid. Accordingly, the invention provides a printing fluid for use in three-dimensional printing wherein the printing fluid comprises glycerin, water, surfactant and at least one organic solvent. The invention also provides a three-dimensional printing method comprising: a) depositing a printing fluid comprising glycerin, water and at least one organic solvent onto at least one layer of powder; and b) reducing the content of water and solvent in the at least one layer, thereby forming a three-dimensionally printed porous matrix. The invention also provides a three-dimensional printing system comprising: a) a layer-forming system that forms layers of powder; and b) a printing fluid deposition system that deposits printing fluid onto the layers of powder, wherein the printing fluid comprises glycerin, water and at least one organic solvent.

In some embodiments, the printing fluid comprises 0 to about 20% wt, >0 to about 15%, >0 to about 10% or >0 to about 5% wt of glycerin. In some embodiments, the matrix comprises 0 to about 2% or >0 to about 1% wt of glycerin In some embodiments, the process of the invention employs a printing fluid comprising at least one or combination of pharmaceutically acceptable solvent for at least one material in the bulk powder and/or in the printing fluid itself. The printing fluid may comprise: a) a solvent for a material in the bulk powder; b) a solvent for a material in the printing fluid; or c) a combination thereof.

Embodiments of the process of the invention include those wherein the printing fluid comprises a solvent for: a) a binder in the bulk powder; b) a binder in the printing fluid; or c) a combination thereof.

The printing fluid can comprise about 75% to about 95%, or about 80% to about 90% % wt of water.

The printing fluid can comprise 0 to about 20%, >0 to about 20%, >0 to about 15%, >0 to about 10%, >0 to about 5% wt of at least one organic solvent. A suitable organic solvent is alcohol. Suitable alcohols include ethanol, methanol, propanol, isopropanol or a combination thereof. In some embodiments, the alcohol is ethanol or isopropanol.

It should be understood that compounds used in the art of pharmaceutics generally serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

One or more of the components of the formulation can be present in its free base or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The invention also provides a method of administering oxcarbazepine to a subject in need thereof. The method comprises: (a) providing a rapidly dispersing, non-compressed matrix dosage form as described herein, and (b) inserting the dosage form into a moisture-containing body cavity, such as the mouth, of a subject in need thereof, the moisture being capable of dissolving the binder and dispersing the dosage form within a time period ranging from about one to about twenty seconds, thereby dispersing the dosage form in the body cavity. In some embodiments, the method further comprises the step of administering the dosage form to the subject, optionally with a sip (small volume) of fluid after the dosage form is placed in the mouth.

The invention also provides a method of treating a disease, disorder or condition that is therapeutically responsive to oxcarbazepine, the method comprising: a) administering to a subject in need thereof a three-dimensionally printed orodispersible matrix as described herein or as made by the process described herein. The matrix comprises oxcarbazepine (in drug-containing particles), a bulk powder, and binder, and the matrix is dispersible in a small volume of fluid. The dosage and administration regimens detailed in the package inserts for FDA approved products containing oxcarbazepine, e.g. TRILEPTAL®, can be followed for administering the instant dosage form.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example 1

Preparation of Drug-Containing Particles

The following process is used to make drug-containing particles of oxcarbazepine. The following ingredients in the amounts indicated are used.

| INGREDIENT | AMT (% WT.) 1 | AMT (% WT.) 2 | AMT (% WT.) 3 | AMT (% WT.) 4 | AMT (% WT.) 5 | AMT (% WT.) 6 |
|---|---|---|---|---|---|---|
| Oxcarbazpine | 67.5 | 67.8 | 65-70 | 65-70 | 66.7 | 65.2 |
| Microcrystalline cellulose | 22.5 | 22.6 | 21-24 | 21.7-23.3 | 22.2 | 21.7 |
| Hydroxypropyl-cellulose | 3.8 | 3.8 | 2.5-5 | 2.6-5 | 2.6 | 4.8 |
| Sodium lauryl sulfate | 2.8 | 1.4 | 1-5 | 1.4-4.2 | 4.1 | 4 |
| Crosscarmellose sodium | 3.4 | 4.4 | 2.4-5 | 2.4-4.5 | 4.3 | 4.2 |

| INGREDIENT | AMT (% WT.) 7 | AMT (% WT.) 8 | AMT (% WT.) 9 | AMT (% WT.) 10 | AMT (% WT.) 11 | AMT (% WT.) 12 |
|---|---|---|---|---|---|---|
| Oxcarbazpine | 70 | 68.6 | 66.4 | 68 | 67 | 68.3 |
| Microcrystalline cellulose | 23.3 | 22.9 | 22.2 | 22.7 | 22.3 | 22.8 |
| Hydroxypropyl-cellulose | 2.7 | 2.7 | 4.9 | 2.6 | 4.9 | 5 |
| Sodium lauryl sulfate | 1.5 | 1.4 | 4.1 | 4.2 | 1.4 | 1.4 |
| Crosscarmellose sodium | 2.5 | 4.5 | 2.4 | 2.4 | 1.4 | 2.4 |

| Material | % (w/w) | Amount per batch (g) |
|---|---|---|
| Oxcarbazepine | 67.5% | 2295.0 |
| Microcrystalline cellulose (Avicel PH101, FMC) | 22.5% | 765.0 |
| Croscarmellose sodium (Ac-Di-Sol SD-711, FMC) | 3.4% | 115.6 |
| Sodium Lauryl Sulfate | 2.8% | 95.2 |
| Hydroxypropyl cellulose (HPC-SL fine, Nisso) | 3.8% | 129.2 |

The drug-containing particles are made by wet granulation at a scale of 4 L to 200 L. The following equipment and operating parameters were used.

| Equipment | Manufacturer | Location | Parameters |
|---|---|---|---|
| High Shear Granulator (GRAL 25) | Collette | Wommelgem, Belgium | Bowl size = 25 L Mixer and chopper on low speed Binder (water) flow rate 95 mL/min |
| Fluid Bed Processor (FLM.3) | Vector | Marion, IA | 50 C. inlet temperature ~40 cfm air flow Dry to LOD 1-2% |
| Comil (197S) | Quadro | Waterloo, Ontario, Canada | 3000 rpm Multiple passes (050G, 016C, 018R) |

All powders were weighed and added to the bowl of the high shear granulator. The dry powder was mixed at low speed for 1 minute. With the mixer and chopper on low speed, water was added at a rate of 95 mL/min for a total of 1164 g water (25.5% of final wet weight). The granulator was stopped once during the process to scrape the bowl. The wet granulation was dried in a fluid bed drier at 50° C. to an LOD of 1-2%. Using a Comil at 3000 rpm, the dried material was milled through a series of screens to reduce the particle size to an acceptable range for 3DP. The milling began through a 050G screen and ended through a 018R screen. For most batches, a pass was made through an intermediate screen (016C) to prevent blinding.

Example 2

Determination of Crystallinity

A differential scanning calorimeter is used to determine the level of crystallinity of materials before and after inclusion in coated particles. The following process for the temperature ramping profile was used.
1. Equilibrate at −10° C.;
2. Ramp 10° C./min to 70° C.;
3. Isothermal for 5 min;
4. Ramp 10° C./min to −20° C.;
5. Equilibrate at −20° C.;
6. Modulate ±0.8° C. every 60 s;
7. Isothermal for 2 min;
8. Ramp 5° C./min to 250° C.;
9. Ramp 5° C./min to −10° C.

Example 3

Preparation of a Three-Dimensionally Printed Orodispersible Dosage Form

The following process is used to prepare a taste-masked three-dimensionally printed orodispersible dosage form comprising a matrix comprising bound drug-containing particles of oxcarbazepine. The ingredients for the printing fluid and the bulk powder are used in the amounts indicated below:

| Printing fluid | I-A |
|---|---|
| Water (% wt) | 85 |
| Glycerin (% wt) | 5 |
| Ethanol (% wt) | 5 |
| Tween 20 (% wt) | 1 |
| Sucralose (% wt) | 2 |

| Bulk powder: | II-A | II-B | II-C | II-D | II-E |
|---|---|---|---|---|---|
| OXC containing particles (% wt) | 55 | 60 | 65 | 75 | 80 |
| Avicel PH101 (% wt) | 4.5 | 4.5 | 4.5 | 4.5 | 4.5 |
| Mannitol (% wt) | 33 | 28 | 23 | 13 | 8 |
| Polyvinypyrrolidone (% wt) | 7 | 7 | 7 | 7 | 7 |
| Silica (% wt) | 0.5 | 0.5 | 0.5 | 0.5 | 0.5 |
| HPC SL (% wt) (hydroxypropylcellulose) | | | | | |

| | II-F | II-G | II-H |
|---|---|---|---|
| OXC containing particles (% wt) | 70 | 70 | 60 |
| Avicel PH101 (% wt) | 19.5 | 9.5 | 9.5 |
| Mannitol (% wt) | 0 | 10 | 20 |
| Polyvinypyrrolidone (% wt) | 10 | 10 | 10 |
| Silica (% wt) | 0.5 | 0.5 | 0.5 |

| | II-L | II-M | II-N | II-O | II-P |
|---|---|---|---|---|---|
| OXC containing particles (% wt) | 70 | 70 | 70 | 60 | 60 |
| Avicel PH101 (% wt) | 9.5 | 0 | 0 | 4.5 | 4.5 |
| Mannitol (% wt) | 13 | 19.5 | 22.5 | 28 | 28 |
| Polyvinypyrrolidone (% wt) | 7 | 10 | 7 | 7 | 0 |
| Silica (% wt) | 0.5 | 0.5 | 0.5 | 0.5 | 0.5 |
| HPC SL (% wt) (hydroxypropylcellulose) | 0 | 0 | 0 | 0 | 7 |

| | II-Q | II-R | II-S | II-T |
|---|---|---|---|---|
| OXC containing particles (% wt) | 63.5 | 63.5 | 63.5 | 63.5 |
| Avicel PH101 (% wt) | 0 | 21 | 11.1 | 21 |
| Mannitol (% wt) | 36 | 15 | 24.9 | 9 |
| Polyvinypyrrolidone (% wt) | 0 | 0 | 0 | 0 |
| Silica (% wt) | 0.5 | 0.5 | 0.5 | 0.5 |
| HPC SL (% wt) (hydroxypropylcellulose) | 0 | 0 | 0 | 6 |

Any three dimensional printer equipment assembly, known or mentioned herein, can be used. An incremental layer of bulk powder of predetermined thickness is spread onto a prior layer of powder, and printing fluid is applied to the incremental layer as droplets according to a predetermined saturation level, line spacing and printing fluid flowrate to bind the particles therein. This two step process is completed until a matrix comprising the target amount of printed incremental layers.

The following printing parameters are used on a Z-Corp lab scale printer (Model Z310). The printer is equipped with a HP-10 printhead and is operated at a scan rate of droplet size of 30-60 μm and line spacing of 450-600 μm. A solid print pattern is used throughout the dosage form. The specified combination of printing fluid formulation and bulk powder formulation is used. A layer thickness of 0.008 to 0.011 inches is used. A saturation of 90 to 116% is used. The printing fluid I-A is used. Many different combinations of the drug-containing particles Nos. 1-12 and bulk powder formulations IIA through II-T are used.

The printed matrix is separated from loose unprinted powder and the printed matrix is dried by any suitable means to reduce the amount of solvent and moisture to a desired level, thereby producing the final 3DP orodispersible dosage form.

The dispersion time, surface texture (smoothness) and hardness of the dosage form are then determined.

Example 4

Preparation of a Taste-Masked Three-Dimensionally Printed Orodispersible Dosage Forms with Varying Architecture Among Incremental Layers The 3DP process described above is followed; however, it can be conducted in several different ways to prepare dosage forms of different architecture varying in hardness and composition of incremental layers. The following processes provide a dosage form having greater hardness in the upper and lower surfaces as compared to the hardness of the interior portion of the dosage form. This tactic helps create sections within a dosage form with different mechanical properties. This approach is used to design dosage forms in which the composition of the top and bottom layers is different from the middle layers. This design allows the dosage forms to have stronger top and bottom layers, thereby increasing hardness and reducing friability, and a large middle portion with lower hardness, which enables the dosage form to disperse rapidly.

Method A:

In this process, the amount of binder deposited in different incremental layers or within different predefined regions within the same incremental layers is varied. The process of Example 3 is followed to prepare these dosage forms, except that the amount of binder, by way of the printing fluid, deposited onto the powder is varied among the incremental powder layers by using printing fluids differing in concentration of binder.

Method B:

The process of Example 3 is followed to prepare these dosage forms, except that the amount of printing fluid deposited onto the powder is varied among the incremental powder layers. The upper and lower incremental layers receive a higher amount of printing fluid and the incremental layers of the middle portion receive a lower amount of printing fluid.

Method C:

In this process, the printing pattern, employed for the upper and lower incremental layers of the dosage form, is a solid pattern (FIG. 3A). The printing pattern for the middle portion of incremental layers is a gray scale (FIG. 3 B).

Method D:

In this process, the printing pattern, employed for the upper and lower incremental layers of the dosage form, is a solid pattern (FIG. 3A). The printing pattern for the middle portion of incremental layers is an annular/hollow high saturation printing with no printing in the area surrounded by the annulus (FIG. 3C).

Method E:

In this process, the printing pattern, employed for the upper and lower incremental layers of the dosage form, is a solid pattern (FIG. 3A). The printing pattern for the middle portion of incremental layers is a combination of interior gray scale printing surrounded by an exterior high saturation printing (FIG. 3D).

Example 5

Characterization of Dosage Forms

The following procedures were used to characterize the three-dimensionally printed solid porous orodispersible matrices.

Friability

The matrices are analyzed for their resistance to breaking using the tablet friability test (USP protocol <1216>). The test employs a VanKel friabilator (model 45-2000, Varian, USA) equipped with a drum having the dimensions of 285 mm in diameter and 39 mm deep, which is rotated at 25 rpm for 100 revolutions. A minimum number of 10 dosage forms are tumbled at each revolution by a curved projection that extends from the middle of the drum to the outer wall. Thus, at each turn the tablets are caused to roll or slide and fall about 130 mm onto the drum or each other. All loose powder is removed from the tablets and they are weighted collectively before and after the 100 revolutions.

Surface Texture

The matrices are inspected visually with or without the aid of a microscope. The surface texture analyzed to determine if it is rough or smooth and whether the edges of indicia on the upper surface and the edges of the perimeter of the dosage form are clean and sharp or rough and jagged.

The matrices exhibited smooth surfaces with clean and sharp edges.

Hardness

The matrices are analyzed for overall hardness as determined by a tablet breaking force assay according to USP <127>($31^{st}$ edition) using a VK 200 tablet hardness tester (Varian, US). The strength or hardness of the dosage forms is measured by a fracture test. A dosage form is centered between the jaws of the tester and force is applied until the dosage form fractures. The load at fracture is returned in kiloponds (kp). A kilopond is a metric unit of force measurement with 1 kp being equivalent to 9.807 Newtons. A minimum number of 6 dosage forms are tested.

The hardness of the dosage forms ranges from about 0.5 to about 5 kP or about 1 to about 3 kP.

Dispersion Time

The matrices are analyzed for dispersion time in aqueous fluid as follows using a Texture Analyzer (TA HP, Texture Technologies, US) equipped with a 5 Kg load cell and a 1.0 inch diameter acrylic probe (Stable Micro Systems). The dosage form is attached to the probe with double-sided adhesive tape. Under a constant 50 g force (Dor et al. in *Pharm. Dev. Technol.* (2000), 5(4), 575-577; and El-Arini et al. in *Pharm. Dev. Technol.* (2002), 7(3), 361-371), the dosage form is immersed in 3 ml of water at room temperature in a flat bottom aluminum weigh boat. The dispersion time test was conducted using the following parameters. A minimum of 5 dosage forms was tested.

| | |
|---|---|
| Test mode | Compression |
| Pre-test speed (mm/sec) | 5 |
| Test speed (mm/sec) | 8 |
| Post-test speed (mm/sec) | 10 |
| Target mode | Force |
| Force (g) | 50 |
| Hold time (sec) | 15 |
| Trigger type | Auto (force) |
| Trigger force (g) | 5 |
| Water volume (ml) | 3 |

The dispersion time observed for the dosage forms is about 10 sec or less or about 5 sec or less.

Bulk Density

The bulk density of the matrix is determined by measuring the weight of a dosage form and dividing that value by the calculated volume of the dosage form. The volume of a dosage form is calculated by measuring its dimensions and using the proper mathematical formula according to the shape of the dosage form. For example, for a cylindrical dosage form, the volume of which is calculated using the form π²*H, wherein r is the radius of the water and H is its height. A dosage form weighing 0.5 g, having a height of 0.6 cm and a diameter of 1.1 cm, has a volume of about 0.57 cm³, and a bulk density of about 0.877 g/cm³, which is equivalent to about 877 mg/ml.

Dissolution of OXC

Dissolution testing is conducted according to the Guidance for Industry (Section 3.3.2; Waiver of In Vivo Bioavailability and Bioequivalence Studies for Immediate-Release Solid Oral Dosage Forms Based on a Biopharmaceutics Classification System. August 2000. Section IIIc, p 7). The method of USP <711> was followed. Dissolution is performed using a USP Apparatus II (paddle) at 50 rpm using 900 mL of the following deaerated dissolution media: (1) 0.1N HCl; (2) 0.05 M sodium acetate, pH 4.5 buffer and (3) 0.05M KH$_2$PO$_4$, pH 6.8 buffer at 37° C.

Example 6

In Vivo Evaluation of Three-Dimensionally Printed Orodispersible Dosage Forms

This method is used to establish efficacy of the dosage form. Single dosage forms comprising oxcarbazepine are administered twice daily to a subject at 12-hour intervals. Administration is done by placing the dosage form in the mouth of the subject and optionally administering a sip (5-20 ml) of fluid to the subject. Within a short period of time, the dosage form disperses in the subject's mouth. Alternatively, the dosage form is dispersed in a minimal amount of fluid and then administered to the subject orally. The total daily dose of oxcarbazepine will typically range from about 300 to 1200 mg. The subject's pharmacokinetic profile is determined using known methods in the art. The subject level of therapeutic response to the dosage form is determined using known methods in the art.

Example 7

Preparation of Three-Dimensionally Printed Rapidly Dispersible Dosage Forms

The 3DP process described above is used to prepare a three-dimensionally printed rapidly dispersible dosage form comprising a matrix comprising bound drug-containing particles of oxcarbazepine. The ingredients for the printing fluid and the bulk powder are used in the amounts indicated below.

| Printing fluid | III-A | III-B |
| --- | --- | --- |
| Water (% wt) | 80-95 | 80-90 |
| Glycerin (% wt) | 0.5-20 | 2-7 |
| Alcohol (% wt) | 0.1-20 | 1-10 |
| Tween 20 (% wt) | 0.01-10 | 1-5 |
| Sucralose (% wt) | 0-10 | 1-5 |
| Binder (% wt) | 0-10 | |

| Drug-containing particles: | IV-A | IV-B |
| --- | --- | --- |
| OXC (% wt) | 55-75 | 60-70 |
| Avicel PH101 (% wt) | 15-35 | 20-30 |
| HPC (% wt) | 0-10 | 2-5 |
| Surfactant (% wt) | 0-10 | 1-5 |
| Croscarmellose (% wt) | 0-10 | >0-5 |

| Bulk powder: | V-A | V-B |
| --- | --- | --- |
| OXC containing particles (% wt) | 55-65 | 55-65 |
| Avicel PH101 (% wt) | 2-15 | 3-12 |
| HPC (% wt) | 0-10 | 0-10 |
| Mannitol (% wt) | 15-40 | 20-35 |
| Polyvinypyrrolidone (% wt) | 0-10 | 5-10 |
| Silica (% wt) | 0.1-1.5 | 0.2-0.7 |

The printing fluid is applied to incremental layers of bulk powder by way of a 3DP process to prepare a three-dimensionally printed orodispersible dosage form comprising a matrix comprising bound drug-containing particles of OXC.

| Final composition | VII-A | VII-B |
| --- | --- | --- |
| Oxcarbazepine (% wt) | 30-40 | 35-45 |
| Microcrystalline cellulose (% wt) | 15-30 | 15-25 |
| Croscarmellose (% wt) | 1-5 | 1-3 |
| Mannitol (% wt) | 10-30 | 15-30 |
| PVP (% wt) | 0-10 | 0-10 |
| HPC (% wt) | 0-12 | 0-10 |
| Colloidal silicon dioxide (% wt) | 0-2 | 0-2 |
| Glycerin (% wt) | >0-20 | >0-5 |
| Surfactant (% wt) | 0-5 | >0-5 |
| Sweetener (% wt) | 0-5 | >0-5 |

As used herein, the term "about" or "approximately" are taken to mean±10%, ±5%, ±2.5% or ±1% of a specified valued. As used herein, the term "substantially" is taken to mean "to a large degree" or "at least a majority of" or "more than 50% of".

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method of preparing a rapidly dispersible porous three-dimensionally printed bound matrix, the method comprising:
    forming drug-containing particles comprising at least one first disintegrant, at least one first binder, at least one surfactant and native particles of drug, wherein the drug-containing particles have an average, mean or median effective particle size and the native particles of drug have an average, mean or median native particle size, and the ratio of average, mean or median effective particle size to average, mean or median, respectively, native particle size ranges from greater than 1:1 to 200:1;
    combining at least one second disintegrant and at least one second binder with said drug-containing particles to form a bulk powder; and three-dimensionally printing said bulk powder to form one or more of said three-dimensionally printed bound matrix.

2. The method of claim 1, wherein the step of forming drug-containing particles comprises granulating the at least one first disintegrant, at least one first binder, at least one surfactant and native particles of drug.

3. The method of claim 1, wherein the step of three-dimensionally printing comprises forming plural stacked incremental layers of said bulk powder and binding particles of said bulk powder.

4. The method of claim 3, wherein the step of binding comprises depositing printing fluid on one or more of said incremental layers according to one or more predetermined patterns.

5. The method of claim 4 further comprising the step of removing or reducing the amount of printing fluid in the matrix.

6. The method of claim 1, wherein the average native particle size is such that not more than 20% wt of the drug is <32 microns, 40-70% wt of the drug is <63 microns, 70-95% wt of the drug is <125 microns, and 100% wt of the drug is <250 microns, and the ratio of average effective particle size to average native particle size is in the range of greater than 1:1 to about 10:1.

7. The method of claim 1, wherein the native particles of drug have an average, mean or median native particle size in the range of about 1 to about 90 microns, about 1 to about 75 microns, about 1 to about 50 microns, about 1 to about 30 microns, about 1 to about 15 microns, about 1 to about 10 microns, about 2 to about 14 microns, about 10 to about 80 microns, about 20 to about 70 microns, about 20 to about 60 microns or about 30 to about 50 microns.

8. The method of claim 1, wherein the drug-containing particles have an average, mean or median effective particle size in the range of about 50 to about 400 microns, about 50 to about 300 microns, about 50 to about 250 microns, about 60 to about 250 microns, about 60 to about 100 microns, or about 75 to about 250 microns.

9. The method of claim 1, wherein:
the drug-containing particles further comprise at least one sweetener and at least one glidant;
the matrix comprises particles bound by said second binder;
the matrix disperses in less than 15 sec in a volume of 15 ml of aqueous fluid; and/or
the content of drug in the matrix is 35-60% wt based upon the total weight of the matrix.

10. The method of claim 9, wherein: a) at least one surfactant is present in an amount of 0.5-7.0% wt based upon the final weight of the matrix; b) the at least one sweetener is present in an amount of 0.01-2.0% wt based upon the final weight of the matrix; c) the at least one first binder and the at least one second binder are together present in an amount of 5-15% wt based upon the final weight of the matrix; d) the at least one first disintegrant and the at least one second disintegrant are together present in an amount of 10-30% wt based upon the final weight of the matrix; and/or e) the at least one glidant is present in an amount of 0-2% wt based upon the final weight of the matrix.

11. The method of claim 1, wherein: a) the native particles of drug possess a bi-modal or multi-modal particle size distribution; b) the drug-containing particles possess a mono-modal, bi-modal or multi-modal particle size distribution; c) the ratio of average, mean or median effective particle size to average, mean, or median, respectively, native particle size ranges from 2:1 to 100:1 or 3:1 to 50:1; or d) a combination of one or more of the above.

12. The method of claim 1 further comprising the step of including at least one second surfactant in the bulk powder.

13. The method of claim 1, wherein the method comprises:
forming drug-containing particles comprising at least one first disintegrant, at least one first binder, at least one surfactant, a first grade of native particles of drug and a second grade of native particles of drug, wherein the drug-containing particles have an average, mean or median effective particle size and the first grade of native particles of drug have an average, mean or median first native particle size and the second grade of native particles of drug have an average, mean or median second native particle size, and the ratio of average, mean or median effective particle size to average, mean or median, respectively, first native particle size ranges from greater than 1:1 to about 5:1, and the ratio of average, mean or median effective particle size to average, mean or median, respectively, second native particle size ranges from about 20:1 to about 50:1;
combining at least one second disintegrant and at least one second binder with said drug-containing particles to form a bulk powder; and
three-dimensionally printing said bulk powder to form one or more of said three-dimensionally printed bound matrix.

14. The method of claim 13, wherein the step of forming drug-containing particles comprises granulating the at least one first disintegrant, at least one first binder, at least one surfactant and native particles of drug.

15. The method of claim 13, wherein the step of three-dimensionally printing comprises forming plural stacked incremental layers of said bulk powder and binding particles of said bulk powder.

16. The method of claim 15, wherein the step of binding comprises depositing printing fluid on one or more of said incremental layers according to one or more predetermined patterns.

17. The method of claim 16 further comprising the step of removing or reducing the amount of printing fluid in the matrix.

18. The method of claim 13 further comprising the step of including at least one second surfactant in the bulk powder.

19. A method of preparing a rapidly dispersible porous three-dimensionally printed bound matrix, the method comprising:
forming drug-containing particles comprising at least one first disintegrant, at least one first binder, and native particles of drug, wherein the drug-containing particles have an average, mean or median effective particle size and the native particles of drug have an average, mean or median native particle size, and the ratio of average, mean or median effective particle size to average, mean or median, respectively, native particle size ranges from greater than 1:1 to 200:1;
combining at least one surfactant, at least one second disintegrant and at least one second binder with said drug-containing particles to form a bulk powder; and
three-dimensionally printing said bulk powder to form one or more of said three-dimensionally printed bound matrix.

20. A method of preparing a rapidly dispersible porous three-dimensionally printed bound matrix, the method comprising:

forming drug-containing particles comprising at least one first disintegrant, at least one first binder, and native particles of drug, wherein the drug-containing particles have an average, mean or median effective particle size and the native particles of drug have an average, mean or median native particle size, and the ratio of average, mean or median effective particle size to average, mean or median, respectively, native particle size ranges from greater than 1:1 to 200:1;

combining at least one second disintegrant and at least one second binder with said drug-containing particles to form a bulk powder; and depositing a printing fluid to said bulk powder to form one or more of said three-dimensionally printed bound matrix, wherein the printing fluid comprises at least one surfactant.

21. The method of claim 1, wherein: a) the hardness of the matrix ranges from about 1 to about 3 kp or about 1 to about 7 kp; b) the matrix disperses in 15 sec or less or 10 sec or less when placed in 15 ml of water or in saliva; c) the matrix comprises about 150 mg to about 600 mg of drug; and/or d) the matrix comprises 10 to 40 three-dimensionally printed incremental layers.

22. The method of claim 1, wherein: a) the content of drug-containing particles in the matrix is 55-85% wt, 60-80% wt or 65-70% wt based upon the total weight of matrix in the final dosage form; b) the content of native particles of drug in the drug-containing particles is 55-85% wt, 60-80% wt or 65-70% wt, based upon the final weight of the drug-containing particles; c) the content of first disintegrant in the drug-containing particles ranges up to 30%, 1-15%, or 2-5% wt, based upon the final weight of the drug-containing particles; d) the content of first binder in the drug-containing particles ranges up to 10%, 1-7%, or 2-5% wt, based upon the final weight of the drug-containing particles; e) the content of surfactant in the bulk powder ranges up to 10%, 1-5%, or 1.4-4.2% wt, based upon the final weight of the bulk powder; and/or f) the drug-containing particles are manufactured by wet granulation.

23. The method of claim 1, wherein the matrix comprises about 150 to about 1200 mg, about 150 mg, about 300 mg, about 450 mg, about 600 mg, about 750 mg, about 900 mg, about 1050 mg or about 1200 of drug.

24. The method of claim 1, wherein: a) the first binder and second binder are independently selected at each occurrence from the group consisting of polyvinylpyrrolidone, mannitol, hydroxypropylcellulose, and a combination thereof; b) the first disintegrant and the second disintegrant are independently selected at each occurrence from the group consisting of microcrystalline cellulose, a combination of two grades of microcrystalline cellulose, croscarmellose, and a combination thereof; or c) a combination of the above.

25. The method of claim 1, wherein: a) the drug-containing particles comprise at least two first disintegrants and at least one binder; b) the matrix comprises at least two second binders and at least one second disintegrant; or c) a combination of any of the above.

26. The method of claim 1, wherein: a) at least one first binder is different than the at least one second binder; b) at least one first disintegrant is different than the at least one second disintegrant; c) at least one first binder is the same as the at least one second binder; d) at least one first disintegrant is the same as the at least one second disintegrant; or e) a combination of any of the above.

* * * * *